(12) United States Patent
Glick et al.

(10) Patent No.: US 10,299,914 B2
(45) Date of Patent: May 28, 2019

(54) HYDROPHILIC IOL PACKAGING SYSTEM

(71) Applicant: Carl Zeiss Meditec Productions, LLC, Ontario, CA (US)

(72) Inventors: Robert E. Glick, Trabuco Canyon, CA (US); Stephen Q. Zhou, Irvine, CA (US)

(73) Assignee: Carl Zeiss Meditec Production, LLC, Ontario, CA (US)

( * ) Notice: Subject to any disclaimer, the term of this patent is extended or adjusted under 35 U.S.C. 154(b) by 378 days.

(21) Appl. No.: 15/179,915

(22) Filed: Jun. 10, 2016

(65) Prior Publication Data

US 2016/0278915 A1 Sep. 29, 2016

Related U.S. Application Data

(62) Division of application No. 14/292,322, filed on May 30, 2014, now abandoned.

(60) Provisional application No. 61/895,184, filed on Oct. 24, 2013.

(51) Int. Cl.
| | |
|---|---|
| *A47C 11/00* | (2006.01) |
| *A61F 2/16* | (2006.01) |
| *B65D 43/00* | (2006.01) |
| *B65D 81/18* | (2006.01) |
| *B65D 81/26* | (2006.01) |
| *B65D 1/34* | (2006.01) |
| *B65D 77/04* | (2006.01) |

(52) U.S. Cl.
CPC .............. *A61F 2/1691* (2013.01); *B65D 1/34* (2013.01); *B65D 43/00* (2013.01); *B65D 77/04* (2013.01); *B65D 81/18* (2013.01); *B65D 81/264* (2013.01)

(58) Field of Classification Search
USPC .......................................................... 206/5.1
See application file for complete search history.

(56) References Cited

U.S. PATENT DOCUMENTS

| | | | | |
|---|---|---|---|---|
| 4,113,088 | A | * 9/1978 | Binkhorst ............. | A61F 2/1691 206/210 |
| 4,326,306 | A | 4/1982 | Poler | |
| 4,508,216 | A | * 4/1985 | Kelman ................ | A61F 2/1691 206/5.1 |
| 4,691,820 | A | * 9/1987 | Martinez ............. | B65D 75/326 206/205 |

(Continued)

FOREIGN PATENT DOCUMENTS

| | | |
|---|---|---|
| EP | 1421917 A2 | 5/2004 |
| WO | 2006102450 A2 | 9/2006 |

(Continued)

OTHER PUBLICATIONS

International Preliminary Report on Patentability (IPRP) issued in related International Application No. PCT/US2014/061701, dated Apr. 26, 2016.

(Continued)

*Primary Examiner* — Jacob K Ackun
(74) *Attorney, Agent, or Firm* — Jeffrey G. Sheldon; Cislo & Thomas LLP

(57) ABSTRACT

A method of maintaining a hydrophilic intraocular lens in a foldable state without immersing the intraocular lens in liquid water includes the step of storing the foldable intraocular lens within a substantially airtight package containing a water reservoir not in direct contact with the lens.

10 Claims, 5 Drawing Sheets

(56) References Cited

U.S. PATENT DOCUMENTS

| | | | |
|---|---|---|---|
| 4,860,885 A * | 8/1989 | Kaufman | A45C 11/005 206/5.1 |
| 5,199,559 A | 4/1993 | Dark | |
| 5,941,390 A | 8/1999 | Franceschi et al. | |
| 6,183,513 B1 | 2/2001 | Guenthner et al. | |
| 6,260,695 B1 * | 7/2001 | Tasber | B65B 25/008 206/499 |
| 6,401,916 B2 | 6/2002 | Sakanishi | |
| 7,275,275 B2 * | 10/2007 | Pankow | A45C 11/005 15/104.92 |
| 7,954,636 B2 * | 6/2011 | Vincent-Aubry | A61F 2/1678 206/364 |
| 8,329,097 B1 | 12/2012 | Kunzler | |
| 9,795,474 B2 * | 10/2017 | Glick | A61F 2/1691 |
| 2001/0017271 A1 * | 8/2001 | Yavitz | A45C 11/005 206/5.1 |
| 2002/0117405 A1 * | 8/2002 | Wang | B65B 25/008 206/5.1 |
| 2003/0204252 A1 | 10/2003 | Paul et al. | |
| 2004/0199174 A1 | 10/2004 | Herberger et al. | |
| 2004/0238392 A1 * | 12/2004 | Peterson | A61F 2/1691 206/438 |
| 2005/0048099 A1 * | 3/2005 | Shiah | A61K 9/0051 424/428 |
| 2006/0037871 A1 * | 2/2006 | Jin | A61F 2/1691 206/5.1 |
| 2006/0260956 A1 * | 11/2006 | Stachowski | B65B 25/008 206/5.1 |
| 2007/0000801 A1 * | 1/2007 | Mauran | A61F 2/1664 206/438 |
| 2007/0034533 A1 | 2/2007 | Coldrey | |
| 2007/0055370 A1 | 3/2007 | Sorochkin et al. | |
| 2007/0250068 A1 | 10/2007 | Vincent-Aubry | |
| 2008/0077237 A1 | 3/2008 | Isaacs et al. | |
| 2008/0147082 A1 | 6/2008 | Pynson | |
| 2009/0057167 A1 * | 3/2009 | Rathert | A61F 2/1691 206/205 |
| 2009/0145091 A1 * | 6/2009 | Connolly | B29D 11/00067 53/467 |
| 2011/0046634 A1 * | 2/2011 | Rathert | A61F 2/1664 606/107 |
| 2011/0144654 A1 | 6/2011 | Isaacs et al. | |
| 2011/0190777 A1 | 8/2011 | Hohl | |
| 2011/0284396 A1 * | 11/2011 | Pugh | A45C 11/005 206/5.1 |
| 2012/0130390 A1 | 5/2012 | Davies et al. | |
| 2012/0296424 A1 | 11/2012 | Betser | |
| 2013/0233736 A1 | 9/2013 | Hess et al. | |
| 2014/0316424 A1 * | 10/2014 | Gulati | A61F 2/167 606/107 |
| 2015/0014187 A1 * | 1/2015 | Gilman | B65D 81/22 206/5.1 |
| 2015/0114855 A1 | 4/2015 | Glick et al. | |
| 2015/0223931 A1 | 8/2015 | Glick et al. | |
| 2015/0297861 A1 | 10/2015 | Passalaqua et al. | |

FOREIGN PATENT DOCUMENTS

| | | |
|---|---|---|
| WO | WO 2013/126174 | 8/2013 |
| WO | 2015061401 A1 | 4/2015 |
| WO | 2015183432 A1 | 12/2015 |

OTHER PUBLICATIONS

United States Patent & Trademark Office, Office Action on the Merits issued in parent U.S. Appl. No. 14/292,322 dated Feb. 10, 2016, 11 pages.

United States Patent & Trademark Office, International Search Report and Written Opinion issued for International Application No. PCT/US14/61701 dated Dec. 31, 2014, 16 pages.

European Patent Office, International Search Report and Written Opinion issued for International Application No. PCT/US2015/027130 dated Jul. 22, 2015, 12 pages.

European Patent Office, Supplementary European Search Report for EP14856145 dated Jul. 27, 2017, 8 pages.

European Patent Office, International Preliminary Report on Patentability (IPRP) issued in related International Application No. PCT/US2015/027130, dated Dec. 6, 2016 (7 pages).

* cited by examiner

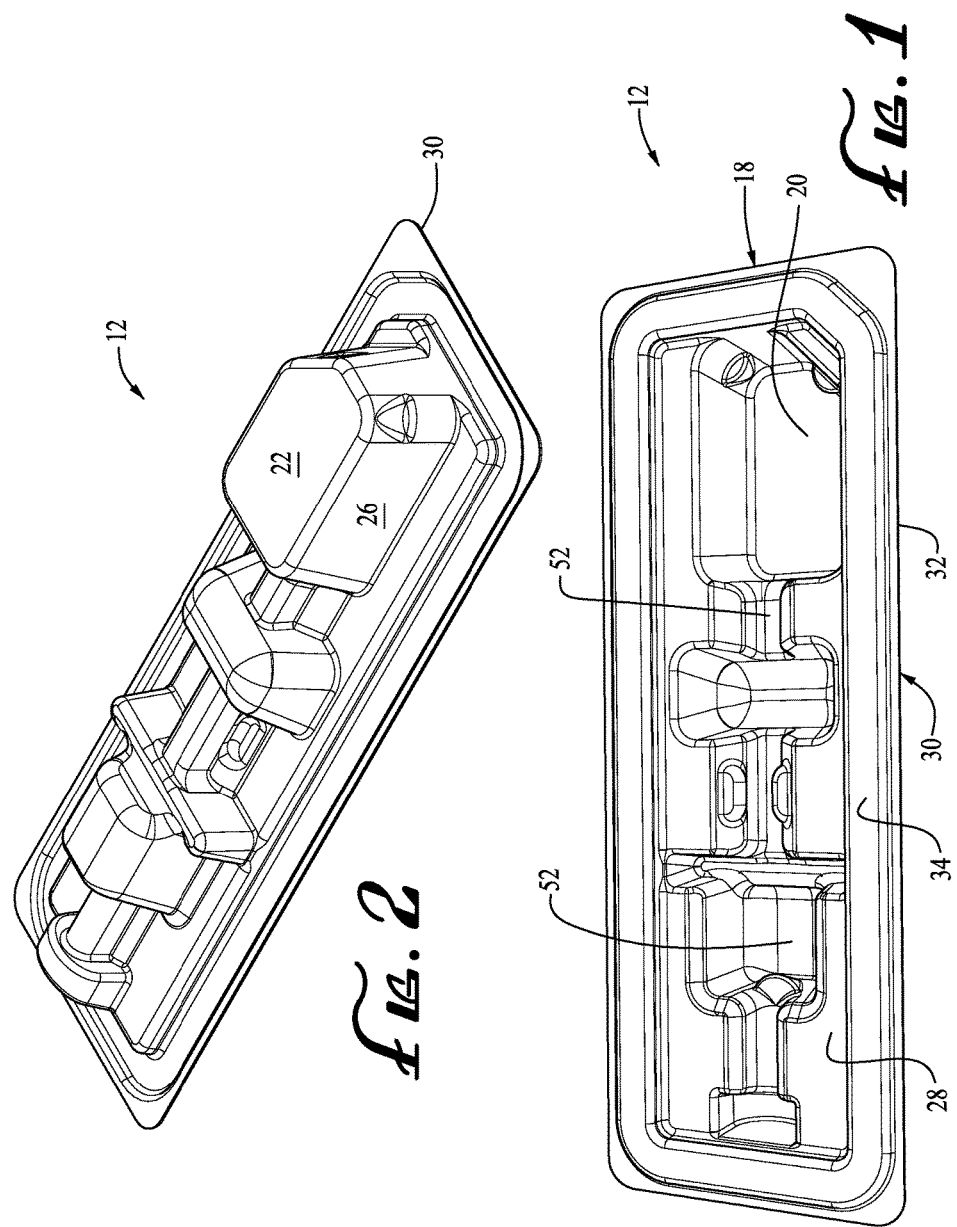

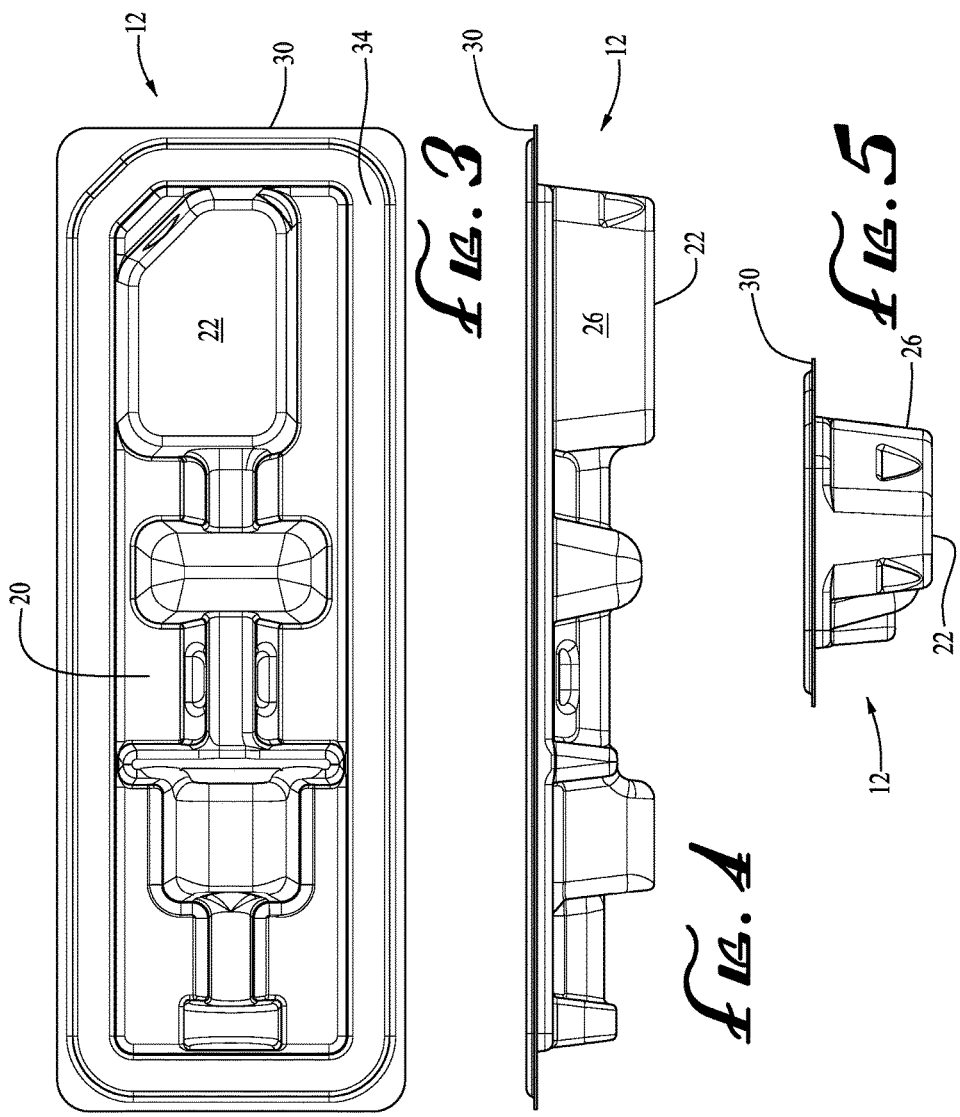

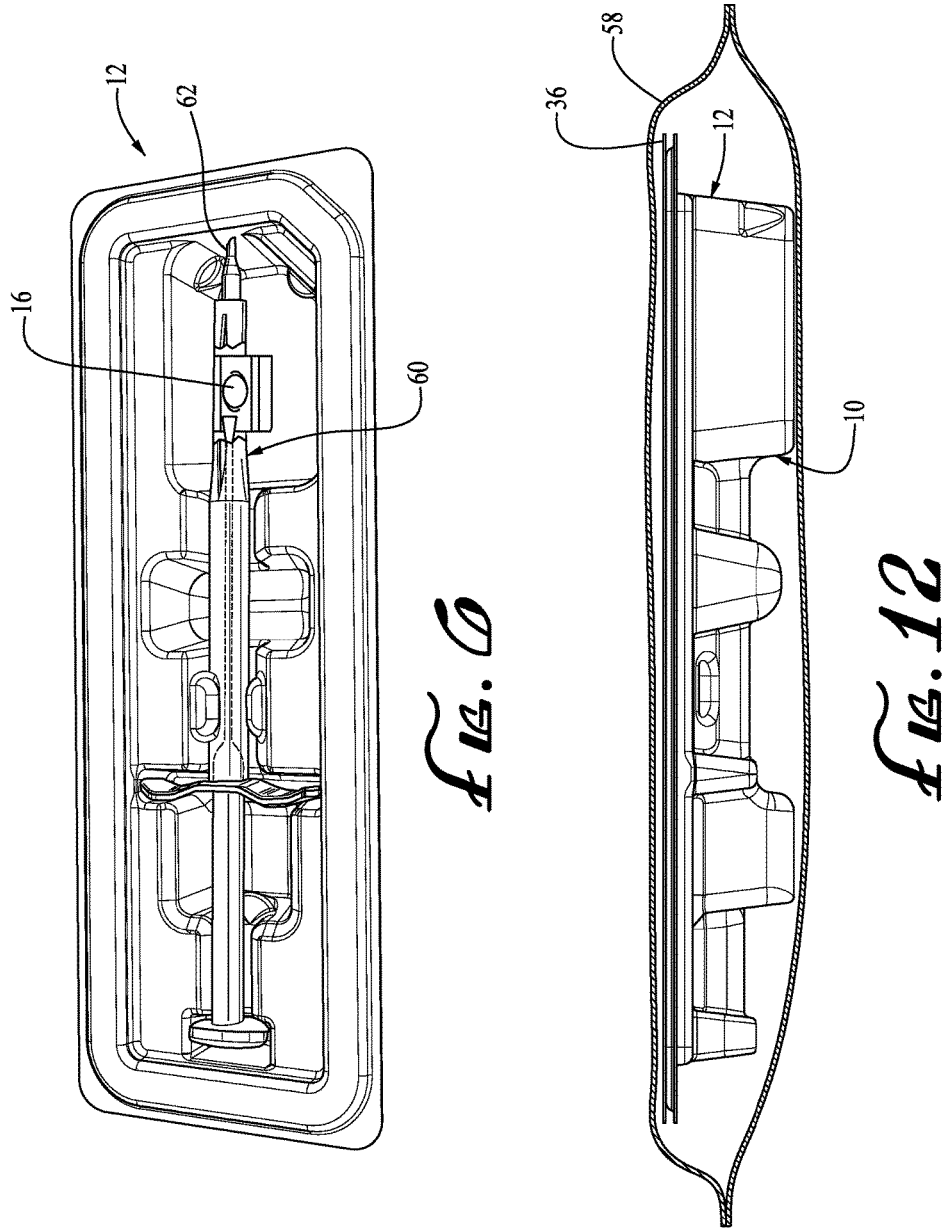

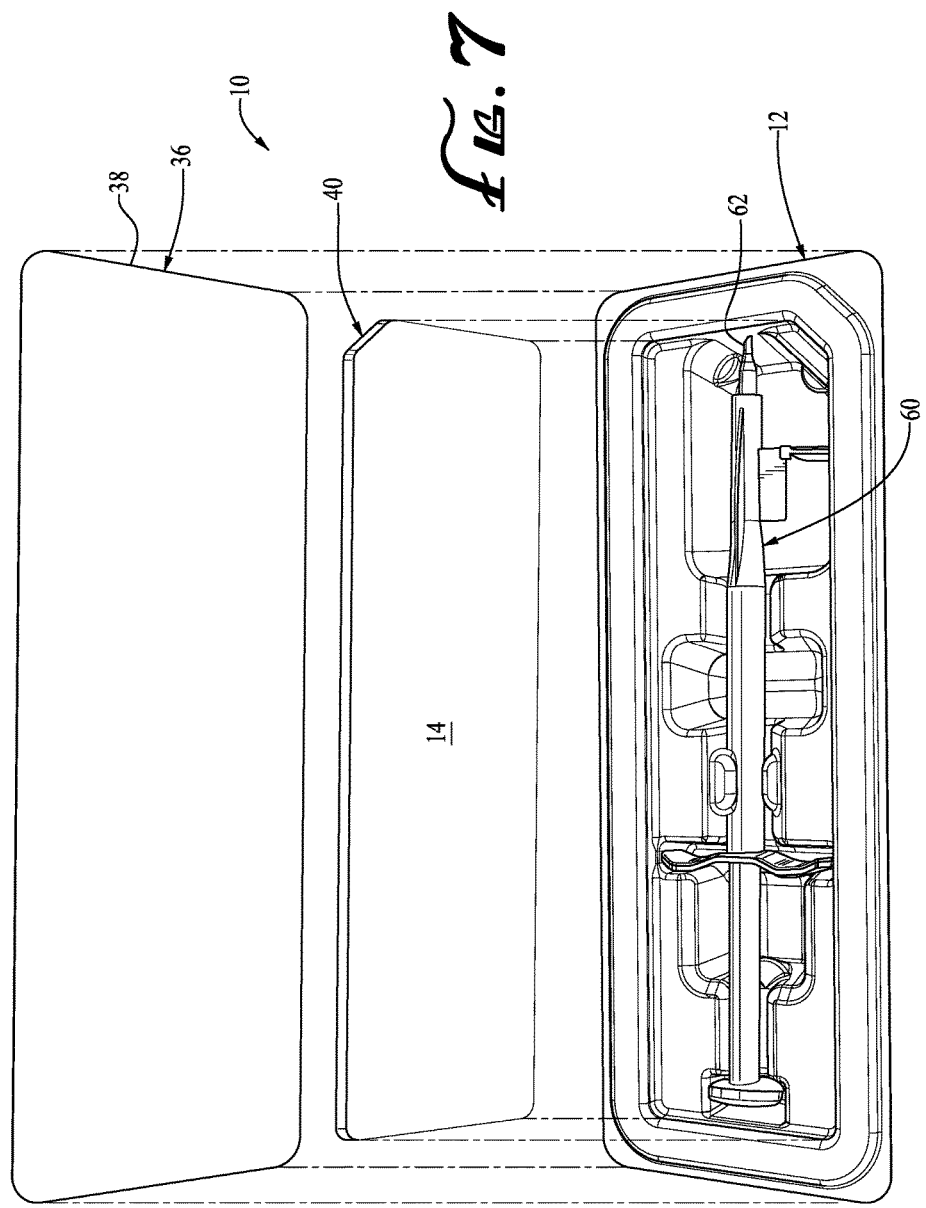

HYDROPHILIC IOL PACKAGING SYSTEM

CROSS-REFERENCE TO RELATED APPLICATIONS

This application is a divisional of U.S. patent application Ser. No. 14/292,322 titled "Hydrophilic IOL Packaging System," filed on May 30, 2014, which claims the benefit of U.S. Provisional Patent Application No. 61/895,184 titled "Hydrophilic IOL Packaging System," filed Oct. 24, 2013, the contents of which are incorporated herein by reference in their entirety.

FIELD OF THE INVENTION

This invention relates generally to packaging methods and systems, and more specifically to packaging methods and systems for foldable intraocular lenses.

BACKGROUND OF THE INVENTION

IOL polymers can be broadly categorized into two groups: (1) materials that absorb less than 1 percent water and (2) materials that absorb more than 1 percent water. Materials that absorb less than one percent water are typically referred to as hydrophobic polymers. Hydrophobic polymers may be foldable at room temperature. Their "foldability" results from their composition rather than from water acting as a plasticizer. Water absorbing polymers are typically referred to as hydrophilic polymers or hydrogels. The most common materials in this group have approximately 25 percent water by weight. Hydrophilic polymers are usually foldable at room temperature by virtue of absorbed water acting as a plasticizer.

The conventional thinking in the intraocular lens (IOL) industry is that hydrophilic IOLs must be immersed in water or saline during storage to maintain a level of hydration needed for foldability at room temperature. Accordingly, lenses composed of these materials are almost always packaged in normal saline (0.9 percent sodium chloride). Such lenses may reside in saline for up to five years prior to implantation. The normal saline, in which these lenses are packaged, is generally designed to mimic the conditions of the anterior segment of the eye where the lens will reside following implantation. This means that lenses will have similar dimension and mechanical characteristics in the eye as they have in the package where they reside prior to implantation.

Immersion in water or saline in the presence of other plastics needed for retention or insertion of the IOL, however, can result in contamination of the IOL by chemical entities contained in or produced by other plastic components in the packaging system. Being immersed in water or saline, the IOL can "communicate" with plastic components via the liquid phase. Also, when an insertion instrument is removed from the package for use, water can flow from where the instrument was stored within the package to the IOL.

The packaging of IOLs in water or saline has the additional disadvantage, especially when the IOL is packaged with an insertion instrument, of increasing the weight of the package, thereby increasing shipping costs.

SUMMARY OF THE INVENTION

The invention avoids the aforementioned problems in the prior art. In one aspect of the invention, the invention is a method of maintaining a hydrophilic intraocular lens in a foldable state without immersing the intraocular lens in liquid water. The method comprises the step of storing the foldable intraocular lens within a substantially airtight package containing a water reservoir not in direct contact with the lens.

In another aspect of the invention, the invention is a combination comprising (a) a substantially airtight container having a water reservoir; and (b) a foldable hydrophilic intraocular lens disposed within the container so as not to be in direct contact with the water reservoir.

DRAWINGS

These and other features, aspects and advantages of the present invention will become better understood with reference to the following description, appended claims, and accompanying drawings where:

FIG. 1 is an upper side perspective view of a container usable in the invention;

FIG. 2 is a lower side perspective view of the container illustrated in FIG. 1;

FIG. 3 is a bottom view of the container illustrated in FIG. 1;

FIG. 4 is a side view of the container illustrated in FIG. 1;

FIG. 5 is an end view of the container illustrated in FIG. 1;

FIG. 6 is a top view of the container illustrated in FIG. 1, showing retention of an IOL and an IOL injector;

FIG. 7 is an exploded perspective view of a combination having features of the invention;

FIG. 12 is a perspective view of the embodiment illustrated in FIG. 7 disposed within a foil pouch.

DETAILED DESCRIPTION OF THE INVENTION

Figure 8:
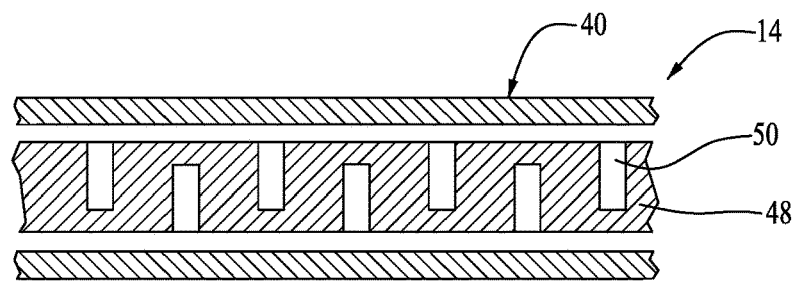
FIG. 8 is a cross-sectional detail view of a first distribution enhancer usable in the embodiment illustrated in FIG. 7.

The following discussion describes in detail one embodiment of the invention and several variations of that embodiment. This discussion should not be construed, however, as limiting the invention to those particular embodiments. Practitioners skilled in the art will recognize numerous other embodiments as well.

Definitions

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers, ingredients or steps.

The Invention

In one aspect of the invention, the invention is a method of maintaining a hydrophilic intraocular lens in a foldable state without immersing the intraocular lens in liquid water. The method comprises the step of storing the foldable intraocular lens within a substantially airtight package containing a water reservoir not in direct contact with the lens.

As used within this application, the word "foldable" means sufficiently pliable to allow the lens to be rolled into a cylinder with an external diameter sufficiently small to permit the lens to be injected into the eye of a patient through an injection tube having a diameter of 2 mm or less. As used herein, the phrase "not to be in direct contact with the lens" means that the water reservoir does not immerse more than the outer edges of the intraocular lens.

The inventors have discovered the surprising fact that sufficient hydration of a hydrophilic lens can be maintained to the extent needed for folding and insertion into an eye without immersion of the lens in a liquid. In the present invention, this is accomplished by packaging the IOL with water saturated air, or nearly saturated air. By "nearly saturated" it is meant a humidity level of at least about 90%, preferably at least 95%. When saturated, such air cannot accept water from a hydrophilic IOL, and when nearly saturated, such air can only accept a minimal amount of water from a hydrophilic IOL. When the air within the container is nearly saturated and the volume of such air within the container is minimal (e.g. less than 100 cubic centimeters), the loss of water from the IOL is unimportantly small.

Moreover, virtually any cycling of temperature within the sealed IOL package during storage results in temperatures which fall below the package interior's dew point and which causes condensation upon the IOL. Even small decreases in the package temperature may cause the air within the package to reach its dew point—thus resulting in condensation on all surfaces within the package, including on those of the IOL. The presence of water droplets on the IOL's surfaces assures a level of hydration adequate for foldability and delivery through a small diameter tube.

In a second aspect of the invention, the invention is a combination 10 comprising (a) a substantially airtight container 12 having a water reservoir 14; and (b) a foldable hydrophilic intraocular lens 16 disposed within the container 12 so as not to be in direct contact with the water reservoir 14. One embodiment of the combination 10 is illustrated in the drawings.

FIGS. 1-5 illustrate a substantially airtight container 12 useable in the invention. By "substantially airtight", it is meant that the container 12 is fully enclosed, but very small amounts of air may diffuse through the container walls.

In the embodiment illustrated in FIGS. 1-5, the container 12 comprises a tray 18 having an elongate compartment 20 bounded by a bottom wall 22, side walls 26 and an elongate top opening 28. In a typical embodiment, the tray 18 can has a length of about 7.8 inches, a width of about 2.75 inches and a maximum depth of about 1.0 inches.

The tray 18 can be made from a thermoplastic, such as polypropylene. In the embodiment illustrated in FIGS. 1-5, the tray 18 can be made from 0.040" polypropylene.

In the embodiment illustrated in FIGS. 1-5, the tray 18 has a circumferential rim 30 with a raised outer lip 32 surrounding a recessed inner band 34.

The elongate top opening 28 is sealed by a cover 36. The cover 36 of the container 12 is typically provided by a foil lid 38, preferably by a multilayered foil lid 38, to minimize the amount of water lost to diffusion.

The water reservoir 14 provides an amount of water which barely exceeds that needed to moisture saturate the interior volume of the container 12 at temperatures up to those needed for steam sterilization, as well as to form small water droplets throughout the container 12. This amount of water should include that which would be lost over the storage duration due to diffusion through the walls of the container 12.

Typically the amount of free water within the container will range from 0.5 to 3 milliliters of water, such as, for example, about 1 milliliter.

The water reservoir 14 can be provided by a variety of one or more devices. In the embodiment illustrated in FIG. 7, the water reservoir 14 comprises water retained within a water permeable pouch 40 disposed below the cover 36. The pouch 40 is designed to capture and retain water which is only released as "free" water when atmospheric and other free water within the container 12 is depleted over time by diffusion through the container walls 22 and 26. Typically, the amount of water captured and retained within the pouch 40 when the container 12 is initially sealed is between about 5 milliliters and about 20 milliliters. The pouch 40 can be made, for example, from a Tyvek®, a material sold by E. I. du Pont de Nemours and Company of Wilmington, Del.

Figure 9:
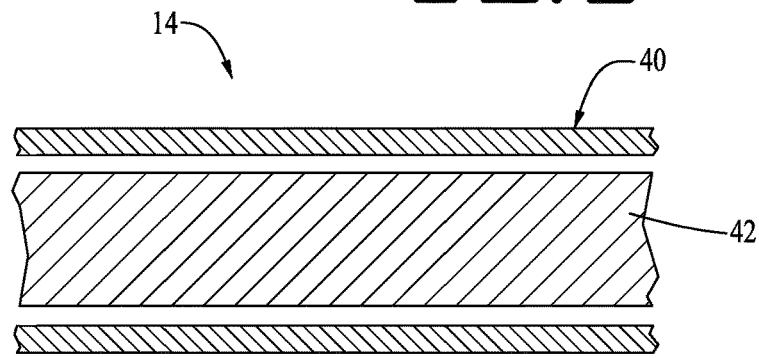
FIG. 9 is a cross-sectional detail view of a second distribution enhancer usable in the embodiment illustrated in FIG. 7.

The pouch 40 effectively minimizes humidity variations throughout the container 12. The pouch 40 may contain distribution enhancers that facilitate distribution of water over the length and width of the pouch 40 regardless of the container's orientation. In one embodiment, the distribution enhancers can be provided by a towel 42 with wicking or sponge-like properties, such as illustrated in FIG. 9.

Figure 10:
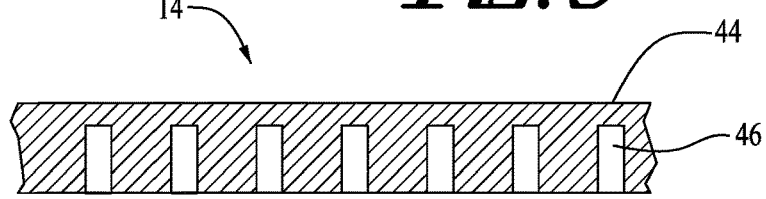
FIG. 10 is a cross-sectional detail view of a third distribution enhancer usable in the embodiment illustrated in FIG. 7.

As illustrated in FIG. 10, the distribution enhancers can also be provided by a piece of plastic 44 that has openings 46 in the form of blind holes (holes defined in one side of the material which do not extend through the material and out the opposite side) that span the surfaces of the tray 18. The blind holes are capable of retaining free water to saturate the vapor phase within the container 12.

As illustrated in FIG. 8, the distribution enhancers can also be provided by a water absorbing polymer 48, such as polyvinyl pyrollidone or polymethacrylic acid, having a high water content that can be released to the atmosphere of the container 12. Preferably, the water absorbing polymer 48 defines holes 50, such as blind holes or through holes in which free water can reside.

As illustrated in FIG. 1, the water reservoir 14 can also be provided by void volumes 52 within the container 12. The void volumes 52 are defined separate from the location within the container 12 of the intraocular lens 16. Preferably, the void volumes 52 are maximized within the container 12 to minimize the potential for humidity gradients within the container 12.

Figure 11:
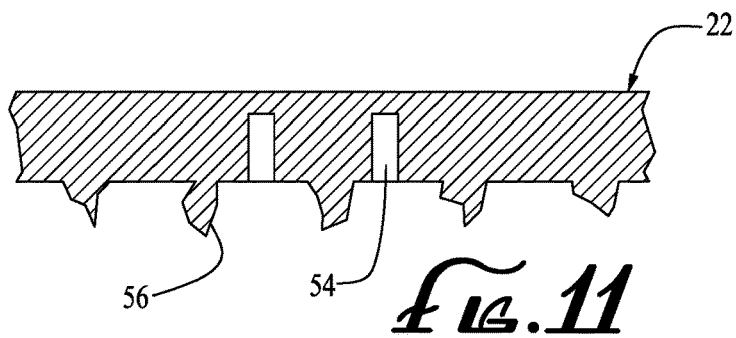
FIG. 11 is a cross-sectional detail view of a fourth distribution enhancer usable in the embodiment illustrated in FIG. 7.

As illustrated in FIG. 11, the water reservoir 14 can also be provided by blind holes 54 in interior surfaces of the tray walls 22 and/or 26 where small quantities of free water can reside. Preferably, the blind holes 54 span a majority of the length and width of the tray.

Also as illustrated in FIG. 11, the water reservoir can also be provided by a non-smooth texture 56 on the interior of surfaces of the tray walls 22 and/or 26 capable of retaining small amounts of free water.

In all cases, the combination 10 is preferably autoclavable—able to withstand being heated to 121° C. or more for period of a half hour or more.

As illustrated in FIG. 12, the combination 10 can be further sealed within an autoclavable foil pouch 58. Such autoclavable foil pouch 58 minimizes the amount of water lost to diffusion, provides a second sterile barrier and allows the container 12 to be introduced into a sterile field.

As illustrated in FIGS. 6 and 7, the intraocular lens 16 can be disposed unfolded within an injector 60, wherein the injector 60 is adapted to fold and inject the intraocular lens 16 into the eye of a patient through a cylindrical injection tube 62 having an inside diameter sufficiently small to allow for surgical implanting of the lens with minimum trauma to the eye. In a typical embodiment the cylindrical injection tube 62 has a diameter of 2 millimeters or less.

Having thus described the invention, it should be apparent that numerous structural modifications and adaptations may be resorted to without departing from the scope and fair meaning of the instant invention as set forth herein above and described herein below by the claims.

What is claimed is:

1. A combination comprising:
   a) a substantially airtight container having a water reservoir, wherein the container comprises a tray having a bottom wall and side walls, the bottom wall and the side walls having interior surfaces, wherein the water reservoir is provided by a plurality of blind holes in the interior surfaces of the bottom wall or the side walls or both the bottom wall and the side walls, wherein free water resides in at least some of the blind holes without any cover on the blind holes; and
   b) a foldable hydrophilic intraocular lens disposed within the container.

2. The combination of claim 1, wherein the water reservoir retains between about 0.5 and 3 ml of water.

3. The combination of claim 1, wherein the combination is disposed within an autoclavable foil pouch.

4. The combination of claim 1, wherein the water reservoir is also provided by non-smooth textures on the interior surfaces and wherein the water reservoir comprises free water retained within at least some of the surfaces with non-smooth textures.

5. The combination of claim 4, wherein water reservoir retains between about 0.5 and 3 ml of water.

6. The combination of claim 4, wherein the combination is disposed within an autoclavable foil pouch.

7. The combination of claim 1, wherein the plurality of blind holes span a majority of the length and width of the tray.

8. A combination comprising:
   a) a substantially airtight container comprising a tray having a bottom wall and side walls, the bottom wall and the side walls having interior surfaces, wherein the container has a water reservoir that is provided by non-smooth textures on the interior surfaces of the bottom wall and the side walls of the tray, and the water reservoir comprises free water retained within at least some of the surfaces with non-smooth textures without a cover on the water reservoir; and
   b) a foldable hydrophilic intraocular lens disposed within the container.

9. The combination of claim 8, wherein the water reservoir retains between about 0.5 and 3 ml of water.

10. The combination of claim 8, wherein the combination is disposed within an autoclavable foil pouch.

\* \* \* \* \*